United States Patent [19]

Hug et al.

[11] Patent Number: 5,760,402
[45] Date of Patent: Jun. 2, 1998

[54] DUAL-HEAD MEDICINE IMAGING SYSTEM WITH CANTILEVERED DETECTOR HEADS

[75] Inventors: Paul Hug, Saratoga; Horace N. Kemp, Walnut Creek; Chinh Quang Le, Milpitas, all of Calif.

[73] Assignee: ADAC Laboratories, Milpitas, Calif.

[21] Appl. No.: 660,807

[22] Filed: Jun. 7, 1996

[51] Int. Cl.⁶ .......................... G01T 1/164; G01T 1/166
[52] U.S. Cl. ................. 250/363.05; 250/363.08
[58] Field of Search ............... 250/363.05, 363.08; 378/15

[56] References Cited

U.S. PATENT DOCUMENTS

| H12 | 1/1986 | Bennett et al. | 250/366 |
|---|---|---|---|
| Re. 29,216 | 5/1977 | Colombo et al. | 250/363.08 |
| 1,599,696 | 9/1926 | Wantz | 378/152 |
| 2,595,260 | 5/1952 | Hollstein . | |
| 3,011,057 | 11/1961 | Anger | 250/71.5 |
| 3,281,598 | 10/1966 | Hollstein . | |
| 3,549,885 | 12/1970 | Anderson . | |
| 3,617,749 | 11/1971 | Masslot . | |
| 3,697,751 | 10/1972 | Grady . | |

(List continued on next page.)

FOREIGN PATENT DOCUMENTS

| 2070464 | 12/1992 | Canada | A61B 6/02 |
|---|---|---|---|
| 0 332 937 A1 | 3/1989 | European Pat. Off. . | |
| 0 465 952 A2 | 1/1992 | European Pat. Off. . | |
| 3145430 A1 | 5/1983 | Germany . | |
| 1175032 | 12/1969 | United Kingdom . | |
| 1540365 | 2/1979 | United Kingdom | G01N 23/06 |
| 1572809 | 8/1980 | United Kingdom . | |
| 2 120 060 | 11/1983 | United Kingdom . | |
| WO 92/07512 | 5/1992 | WIPO . | |

OTHER PUBLICATIONS

Stefan P. Mueller, et al.; *Collimator Selection for SPECT Brain Imaging: The Advantage of High Resolution;* The Journal of Nuclear Medicine, vol. 27, No. 11, Nov. 1896; pp. 1729–1738.

Robert L. Eisner; *Principles of Instrumentation in SPECT;* Journal of Nuclear Medicine Technology, vol. 13, No. 1, Mar. 1995; pp. 23–31.

John W. Keyes, Jr., M.D.; *Computed tomography in nuclear medicine;* Lieberman, D.E., Computer Methods, C. V. Mosby Co., St. Louis, 1977; pp. 130–138.

Bernard E. Oppenheim, et al.; *Single Photon Emission Computed Tomography;* Effective Use of Computers in Nuclear Medicine; pp. 31–74.

Sopha Medical; *The New Geometry in Nuclear Medicine;* Sopha Medical Systems, Inc., 7155 Columbia Gateway Drive, Columbia, MD.; 3 pages.

(List continued on next page.)

*Primary Examiner*—Michael J. Tokar
*Assistant Examiner*—Richard Hanig
*Attorney, Agent, or Firm*—Blakely, Sokoloff, Taylor & Zafman LLP

[57] ABSTRACT

A dual-head gamma camera imaging system comprises a master ring gear and a slave ring rotatable about a longitudinal axis. The master ring gear is rotatably supported by a gantry. The slave ring is rotatably supported by the master ring gear and concentric with the master ring gear, such that the master ring gear and the slave ring can be rotated independently about s longitudinal axis. A first detector is supported by a first cantilever support member mounted to the master ring gear. A second detector head is supported by a second cantilever support member mounted to the slave ring. The angular displacement between the detector heads can be varied by providing relative rotation between the master ring gear and the slave ring. The rotation can be accomplished by using the weight of one of the detector heads to hold that detector head stationary while rotating the other detector head using a motor. The imaging system also includes a mechanism for rotating a detector head about an axis perpendicular to its imaging surface to increase the field of view along the longitudinal axis. The detector is mounted to an inner support ring which is rotatably coupled to and concentric with an outer support ring. The outer support ring is mounted to at least one ring gear.

29 Claims, 10 Drawing Sheets

U.S. PATENT DOCUMENTS

| | | | |
|---|---|---|---|
| 3,735,132 | 5/1973 | Carugati et al. | 250/363.08 |
| 3,756,549 | 9/1973 | Lange | 248/123 |
| 3,845,308 | 10/1974 | Cattrell | 250/363 |
| 3,852,601 | 12/1974 | Casale | 250/366 |
| 3,870,886 | 3/1975 | Casale | 250/367 |
| 3,976,885 | 8/1976 | Brunnett et al. | 250/363.08 |
| 4,049,966 | 9/1977 | Luitwieller, Jr. | 250/369 |
| 4,057,727 | 11/1977 | Muehllehner et al. | 250/363 S |
| 4,064,441 | 12/1977 | Casale | 250/363.08 |
| 4,150,297 | 4/1979 | Boggren . | |
| 4,216,381 | 8/1980 | Lange | 250/363.05 |
| 4,223,222 | 9/1980 | Gray et al. | 250/363 S |
| 4,368,389 | 1/1983 | Blum | 250/363.05 |
| 4,400,620 | 8/1983 | Blum | 250/363 S |
| 4,401,890 | 8/1983 | Blum | 250/363 S |
| 4,426,725 | 1/1984 | Grady | 378/196 |
| 4,445,035 | 4/1984 | Ueyama | 250/363.04 |
| 4,476,389 | 10/1984 | Ueyama et al. | 250/363 S |
| 4,503,331 | 3/1985 | Kovacs, Jr. et al. | 250/363 S |
| 4,613,122 | 9/1986 | Manabe | 269/322 |
| 4,645,933 | 2/1987 | Gambini et al. | 250/363 S |
| 4,652,758 | 3/1987 | Barfod | 250/363 S |
| 4,652,759 | 3/1987 | Platz | 250/363 S |
| 5,349,190 | 9/1994 | Hines et al. | 250/363.05 |
| 5,367,169 | 11/1994 | Pierfitte | 250/363.05 |
| 5,444,252 | 8/1995 | Hug et al. | 250/363.8 |
| 5,523,571 | 6/1996 | Velazquez et al. | 250/363.05 |
| 5,594,251 | 1/1997 | Fleury et al. | 250/363.05 |

OTHER PUBLICATIONS

Chun Bin Lim, et al.; *Performance Analysis of Three Camera Configurations for Single Photon Emission Computed Tomography;* IEEE Transactions on Nuclear Science, Feb. 1980; pp. 559–568.

Hugh F. Stoddart, et al.; *A New Development in Single Gamma Transaxial Tomography Union Carbide Focused Collimator Scanner;* IEEE Transactions on Nuclear Science, 1979; pp. 2710–2712.

Stephen C. Gottschalk, et al..; *SPECT Resolution and Uniformity Improvements by Noncircular Orbit;* The Journal of Nuclear Medicine, vol. 24, No. 9; 1983, pp. 822–828.

GE Medical Systems; Optima; GE Medical Systems—Americas; 3 pages.

FIG. 7A
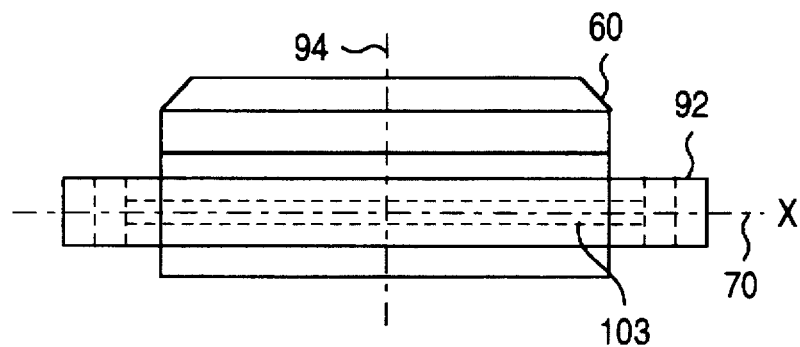
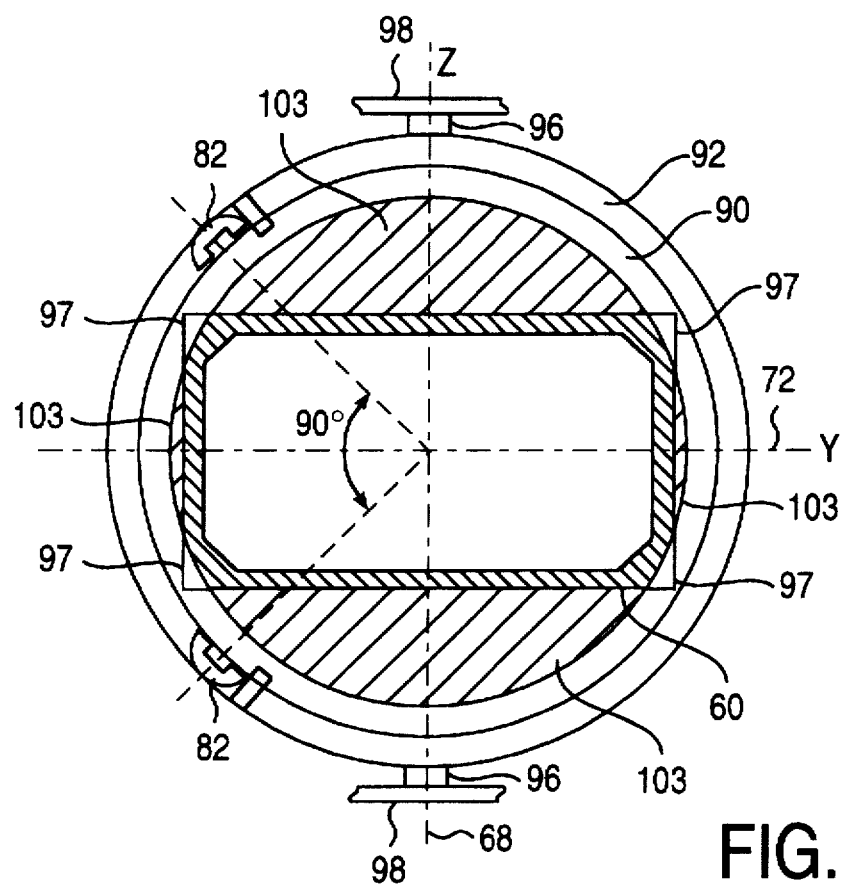
FIG. 7B

FIG. 7C
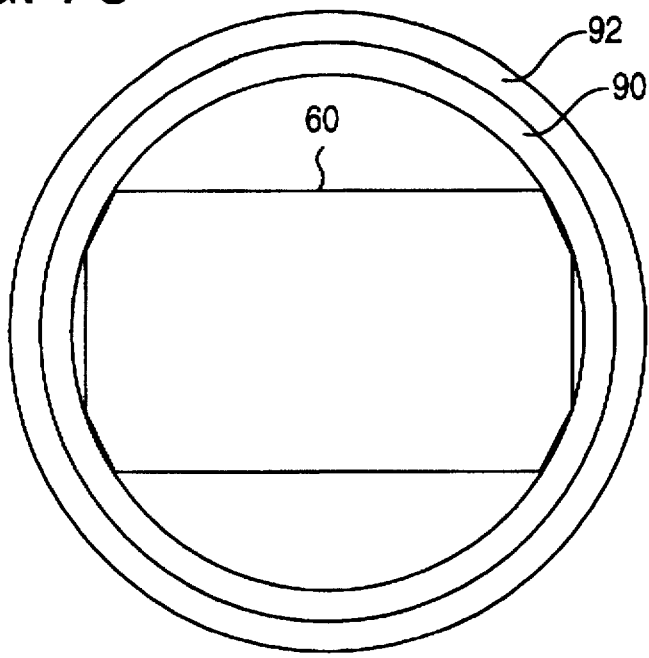
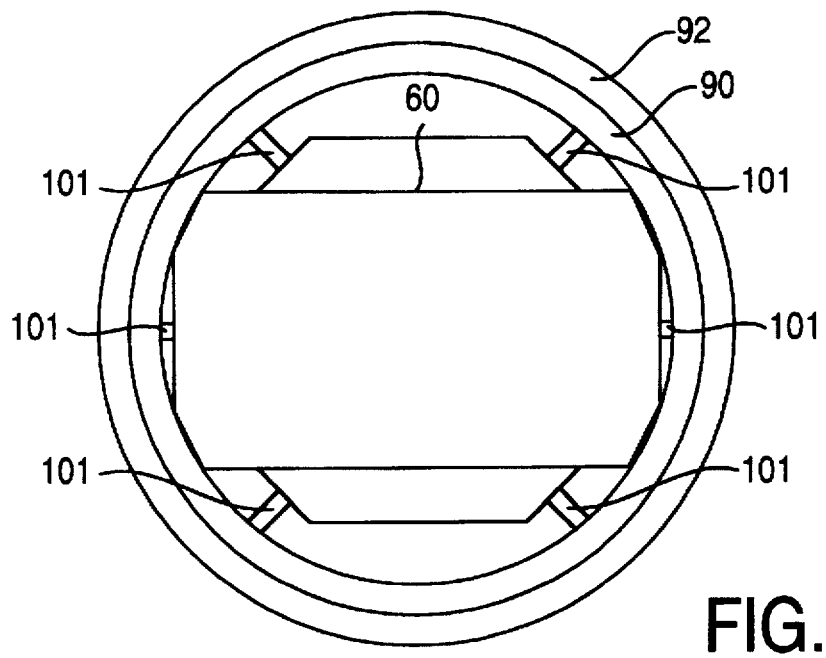
FIG. 7D

5,760,402

1

DUAL-HEAD MEDICINE IMAGING SYSTEM WITH CANTILEVERED DETECTOR HEADS

FIELD OF THE INVENTION

The present invention pertains to the field of medical imaging systems. More particularly, the present invention relates to apparatus for supporting detector heads of a gamma camera.

BACKGROUND OF THE INVENTION

In nuclear medicine imaging techniques such as single-photon emission computed tomography (SPECT) and positron emission tomography (PET), medical images are generated based on gamma rays emitted from the body of a patient after the patient has been injected with a radiopharmaceutical substance. Emitted gamma rays may be detected from numerous different angles around a longitudinal axis of the patient by a gamma camera (i.e., Anger camera or scintillation camera) and then converted into electrical signals that are stored as data. This data is then converted into a set of tomographic images in a process known as image "reconstruction".

Many gamma camera systems use two or more detector heads which are designed to acquire image data simultaneously. In a two-head system, the detectors may be oriented 180 degrees apart relative to a longitudinal axis, as shown in FIG. 1A. For various reasons, however, it is advantageous to be able to change the relative location of the detectors about the longitudinal axis; that is, it is advantageous to be able to vary the angular displacement between the detectors. For example, it is useful in certain diagnostic scenarios to orient the detectors into a 90 degree relative orientation, as shown in FIG. 1B, so that the imaging surfaces of the detectors are perpendicular to each other. Cardiac imaging is one such situation in which such an orientation might be desirable. A gamma camera imaging system which is capable of providing the above-described relative motion between detectors is described in U.S. Pat. No. 5,444,252, which is issued to P. Hug et. al. and assigned to the assignee of the present patent application.

However, another concern in gamma camera systems is patient comfort. In particular, the support structures for gamma camera systems, referred to as the "gantry", are often constructed so that the space in which a patient is situated during imaging is quite small and enclosed from the point of view of many patients. FIG. 2, for example, shows an existing gantry in which two detectors are each supported from two ring-shaped supports. During imaging, the patient is placed with his or her body in a prone position through the two support rings. The support rings create a partial enclosure in which patients often feel anxious or agitated if required to remain in such a position for long periods of time.

Another concern in gamma camera systems is data throughput. Specifically, it is desirable to have the capability to acquire large amounts of image data in a short period of time. Such capability may be crucial in emergency diagnostic situations. In non-emergency situations, such capability reduces the amount of time patients must remain in an uncomfortable position. Generally, in tomographic imaging techniques, images are taken of an area of interest from various angles around the longitudinal axis at a number of positions along the longitudinal axis. For example, in a two-detector system such as that shown in FIG. 2, two rectangular detectors each may be rotated 180 degrees about the longitudinal axis while detecting gamma rays. When one 180-degree rotation is complete, the patient is moved so that the detectors are located at the next position along the longitudinal axis and a second rotation is performed; this process is repeated until the entire area of interest has been imaged. The number of positions along the longitudinal axis that is required depends upon the field of view of the detectors along the longitudinal axis; a larger field of view along the longitudinal axis will permit fewer positions to be used and, therefore, less time to be consumed.

Hence, what is needed is a support structure for a gamma camera system that is both capable of varying the angular displacement between multiple detectors and which provides for greater patient comfort during imaging. What is further needed is a gamma camera system that is capable of increasing throughput and reducing total imaging time.

SUMMARY OF THE INVENTION

A multi-head medical imaging system is provided. The system comprises a support structure and a master ring gear rotatably supported by the support structure, such that the master ring gear is rotatable about a longitudinal axis. A first support member supports the first detector head and is coupled to the master ring gear. The first detector head is supported entirely through the first support member. A slave ring is rotatably coupled to and supported by the master ring gear. A second support member supports the second detector head and is coupled to the slave ring. The second detector head is supported entirely through the second support member. The master ring gear and the slave ring are rotatable about the longitudinal axis, either independently or in unison, such that the first detector head and the second detector head are moveable in rotation about the longitudinal axis relative to each other.

In another aspect of the present invention, a support apparatus for an imaging system detector head is provided. The support apparatus comprises a first support ring and a second support ring. The second support ring is concentric with the first support ring and rotatably coupled to the first support ring. Further, the second support ring has an outer diameter substantially equal to an inner diameter of the first support ring. The detector head has an imaging surface and an axis of rotation passing through the imaging surface perpendicular to the imaging surface. The detector head is mounted to the second support ring, such that the detector is rotatable about the axis of rotation.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which:

FIGS. 7A and 7B illustrate views of a thin-section bearing comprising an inner support ring and an outer support ring.

FIG. 7C illustrates a detector head having tapered corners supported by a thin-section bearing.

FIG. 7D illustrates a detector head coupled to a thin-section bearing by support struts.

DETAILED DESCRIPTION

A dual-head medical imaging system with cantilevered detector heads is described. In the following description, for purposes of explanation, numerous specific details are set forth in order to provide a thorough understanding of the present invention. It will be evident, however, to one skilled in the art that the present invention may be practiced without these specific details.

U.S. Pat. No. 5,444,252 is hereby incorporated by reference into this description.

Figure 3:
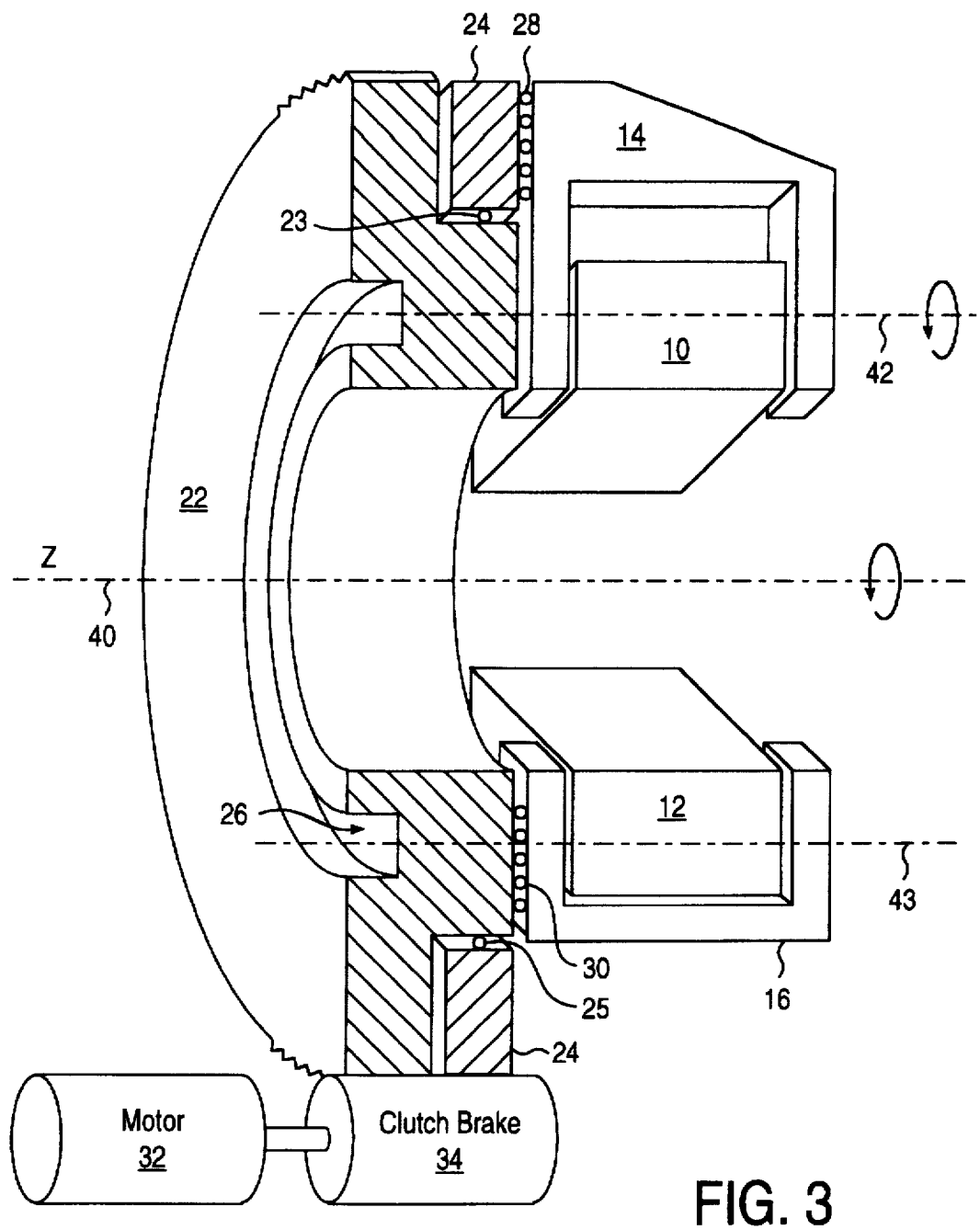
FIG. 3 illustrates a dual-head gamma camera imaging system with two cantilevered detector heads.

FIG. 3 shows a dual-head gamma camera imaging system with cantilevered detector heads. A cantilever support member 16 is coupled to a master ring gear 22 by a vertical radial slide 30. Another cantilever support member 14 is coupled to a slave ring 24 through another vertical radial slide 28. A detector head 10 containing a scintillation detector is mounted to cantilever support member 14. Detector head 10 is rotatable about an axis 42 passing through detector head 10 parallel to a longitudinal (z) axis 40. Another detector head 12, also containing a scintillation detector, is mounted to cantilever support member 16. Detector head 10 is supported entirely through cantilever support member 14, while detector head 12 is supported entirely through cantilever support member 16. It should be appreciated that some form of counterbalance may be required to offset the weight of detector heads 12 and 10 applied to master ring gear 22 and slave ring 24, respectively.

Radial slides 28 and 30 allow the detector heads 10 and 12, respectively, to be independently moved toward or away from the z axis 40. In one embodiment, radial slides 28 and 30 each consist of a number of circulating balls. If desired, a different support member (e.g., similar to cantilever support member 14) may be substituted for cantilever support member 16 in order to provide capability to rotate detector head 12 about an axis 43 passing through detector head 12 parallel to the z axis 40.

Figure 1A:
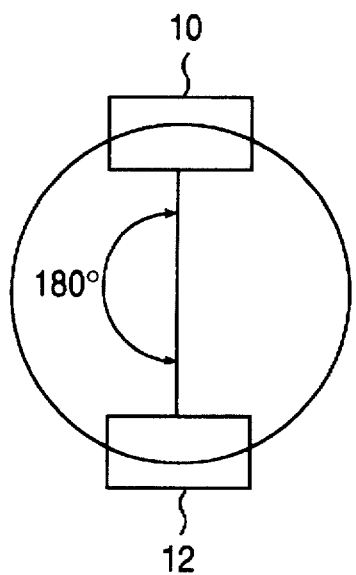
FIGS. 1A and 1B illustrate two orientations of a pair of gamma camera detectors according to the prior art.
Figure 1B:
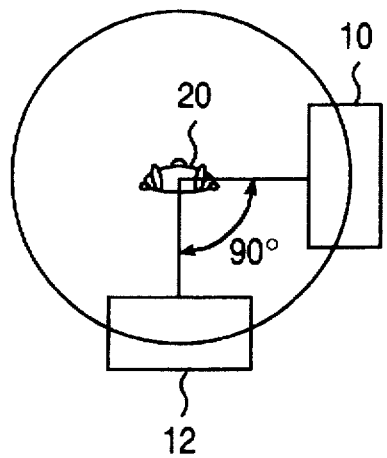
Figure 2:
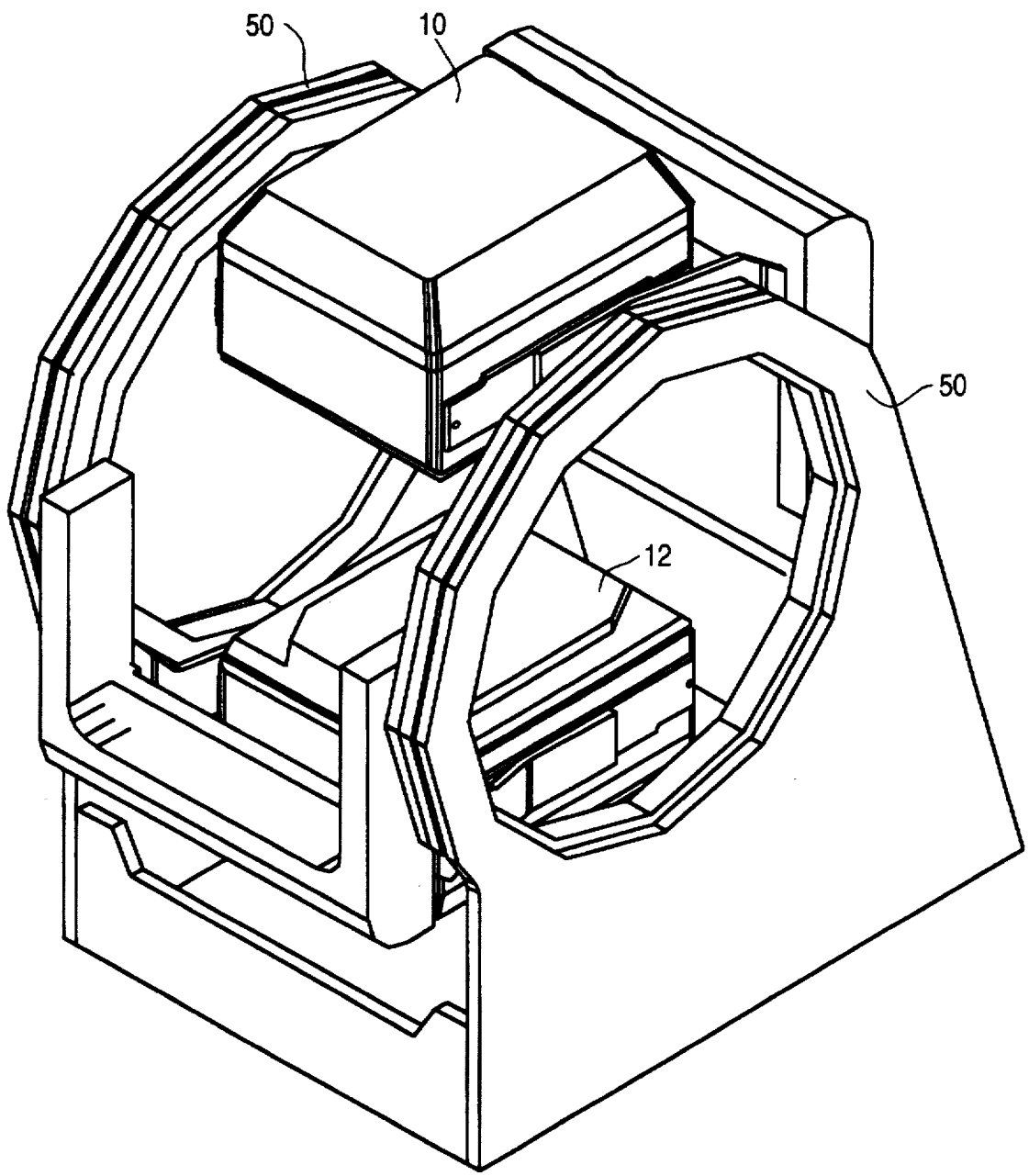
FIG. 2 illustrates a gamma camera system having two detectors according to the prior art.

Master ring gear 22 is supported by a gantry (not shown) such that master ring gear 22 is rotatable about the z axis 40. Slave ring 24 is concentric with master ring gear 22 and is supported by master ring gear 22 through needle bearings 23 and 25. Needle bearings 23 and 25 allow master ring gear 22 and slave ring 24 to be rotated independently about the z axis 40, such that the angular displacement between detector head 10 and detector head 12 can be varied. Specifically, detector heads 10 and 12 can be rotated about the z axis over a range of angular displacements from 180 degrees, as shown in FIG. 1A, to 90 degrees, as shown in FIG. 1B.

The motor 32 drives both master ring gear 22 and slave ring gear 24 via clutch brake 34. Clutch brake 34 provides a mechanism for switching between two mechanical states.

In the first state, master ring gear 22 and slave ring gear 24 are rotatable only in unison (i.e., in synchronous rotation). In the second state, either master ring gear 22 or slave ring 24 is held in place while the other is rotated under power from the motor 32 about the z axis 40 in order to change the angular displacement between the detector heads 10 and 12.

In an alternative embodiment, the second mechanical state is characterized by master ring gear 22 being coupled to the motor 32 via clutch brake 34, while slave ring 24 is uncoupled from the motor 32 and uncoupled from master ring gear 22. In such an embodiment, the angular displacement between detector heads 10 and 12 can be changed by using the weight of detector head 10 (which is coupled to slave ring 24) to hold detector head 10 in position, while the position of detector head 12 is changed by driving master ring gear 22 using the motor 32. More specifically, detector heads 10 and 12 are first arranged so that detector head 12 is in the 12 o'clock position (at the top of the gantry) and detector head 10 is in the six o'clock position (at the bottom of the gantry). Next, the locking mechanism in the clutch brake is disengaged, so that master ring gear 22 and slave ring 24 are decoupled from each other. Master ring gear 22 is then driven through a 90 degree rotation using the motor 32 until detector head 12 is in the 9 o'clock position. A stop exactly 90 degrees from the original position prevents detector head 12 from rotating more than 90 degrees. Detector head 10, which is in the six o'clock position, stays in place due to its own weight. Once the stop has been reached, the locking mechanism is engaged to couple slave ring 24 to the motor 32 and to master ring gear 22, so that detector heads 10 and 12 can move in unison in the 90-degree orientation.

Figure 4:
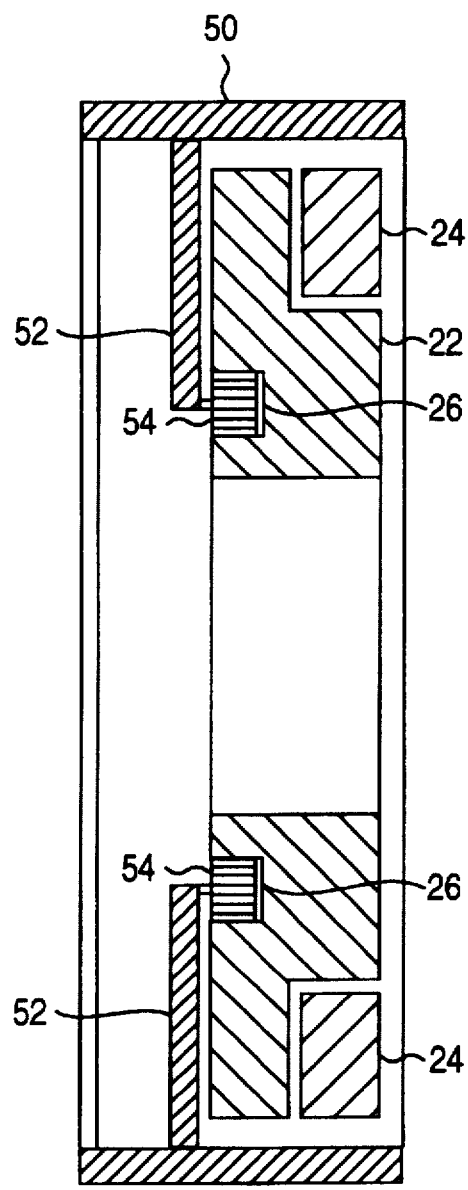
FIG. 4 illustrates a cross section of a structure for supporting cantilevered detector heads.

FIG. 4 illustrates a cross-sectional view of a gantry 50 to illustrate the manner in which the master ring gear 22 is supported by the gantry 50. A groove 26 is provided in master ring gear 22. The groove accommodates a number of rollers 54. Each of the rollers 54 is in contact with groove 26 and is rotatably coupled to one of several support arms, such as support arms 52. Each roller 54 is rotatable about an axis parallel to the z axis 40. Each support arm 52 is fixed to the gantry 50 to protrude radially toward the z axis 40. In the currently preferred embodiment, six support arms 52 and six rollers 54 are used, although only two of each are shown in FIG. 4. Thus, master ring gear 22 is supported by gantry 50 through support arms 52. The rollers 54 allow rotation of master ring gear 22 about the z axis 40.

Figure 5A:
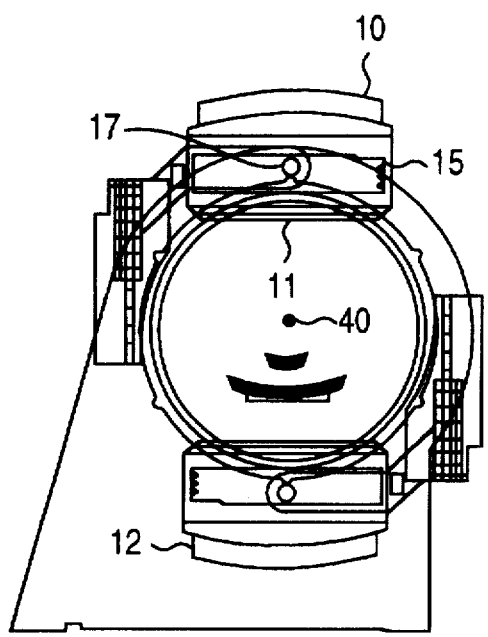
FIGS. 5A through 5D illustrate positions of two detector heads during the positioning of one of the detector heads into an "outer room" position.
Figure 5B:
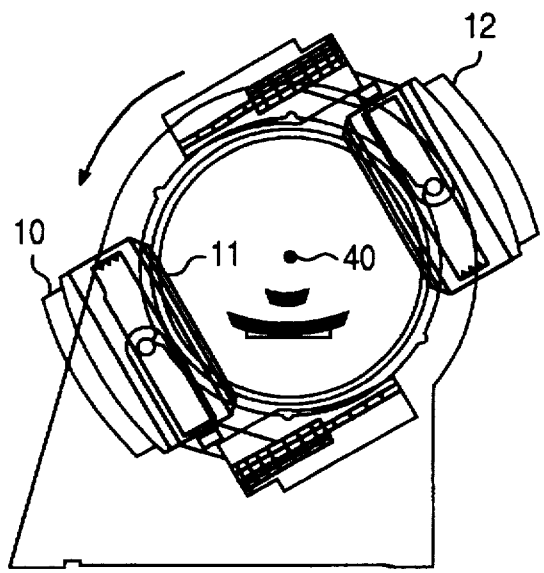
Figure 5C:
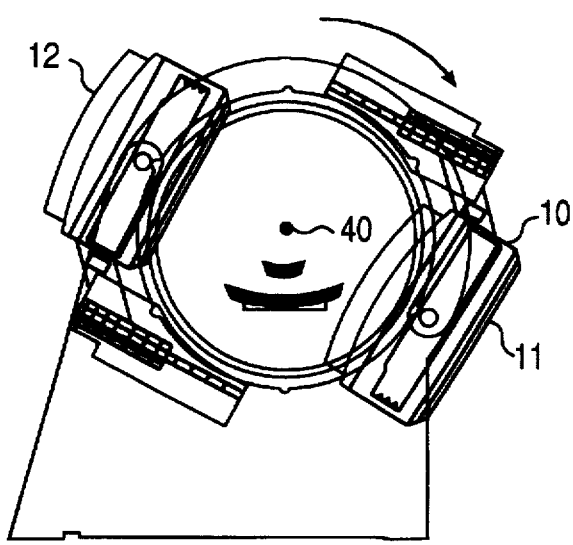
Figure 5D:
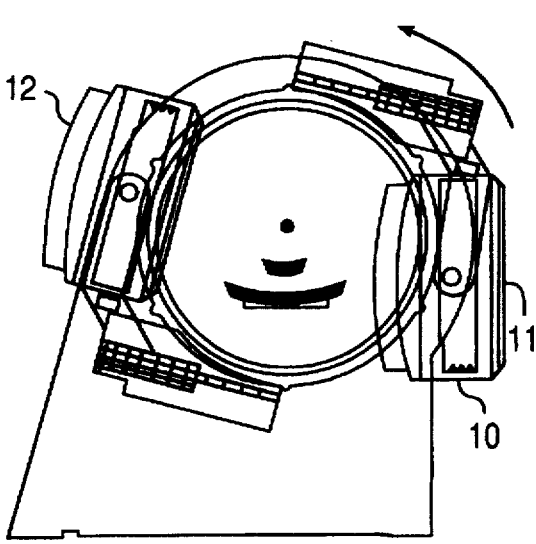

In one embodiment of the present invention, detector head 10 can be rotated about axis 42 (see FIG. 3) into an "outer room position" in which its detector surface 11 faces away from the z axis 40, as shown in FIG. 5D, rather than the normal position in which the detector surface 11 faces the z axis 40, as shown in FIG. 5A. (As mentioned above, axis 42 passes through detector head 10 parallel to the z axis 40.) In the outer room position, a patient need not be positioned inside the gantry to perform imaging. For example, the patient may be imaged while sitting in a chair next to the gantry.

To perform the rotation into the outer room position, gravity is used to provide the necessary rotational force. The detector head 10 is first placed in the 12 o'clock (top) position, as shown in FIG. 5A. In the embodiment of FIGS. 5A through 5D, detector head 10 is suspended from a support member 15 on two sides by low friction bearings 17 to allow rotation of the detector head 10 about axis 42. The suspension is chosen such that the center of mass of detector head 10 is below axis 42 when detector head 10 is in the 12 o'clock position. Referring now to FIG. 5A, with detector head 10 in the 12 o'clock position, master ring gear 22 and slave ring 24 are then rotated 120 degrees counterclockwise. A locking mechanism, which normally prevents rotation of the detector head 10 about axis 42, is then unlocked. The detector head 10 is then free to rotate about axis 42; accordingly, gravitational force causes detector head 10 to rotate about axis 42 such that its center of mass stays below the axis 42. Master ring gear 22 and slave ring 24 are then rotated 240 degrees clockwise, as shown in FIG. 5C, and the locking mechanism is locked to prevent any further rotation of detector head 10 about axis 42. Master ring gear 22 and slave ring 24 are then rotated counterclockwise 15 degrees to bring detector head 10 into the outer room position, as shown in FIG. 5D. In the outer room position, in which the detector surface 11 is perpendicular to the floor and facing away from the z axis 40.

Figure 6A:
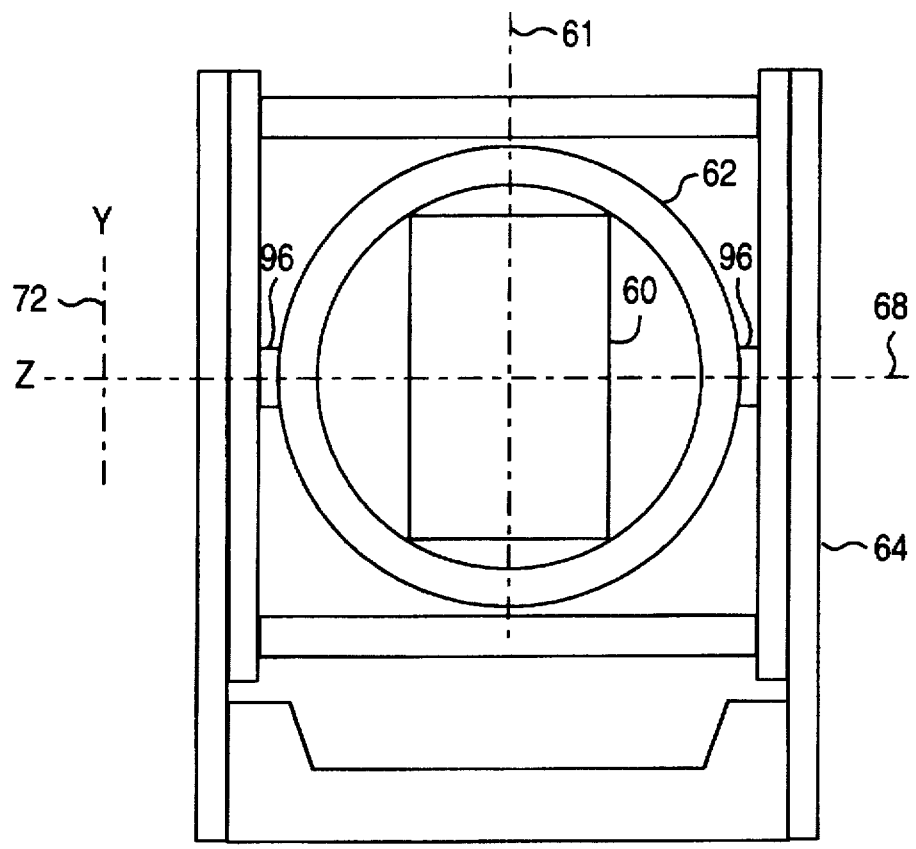
FIGS. 6A and 6B illustrate two different orientations of a detector head supported by a thin-section bearing.
Figure 6B:
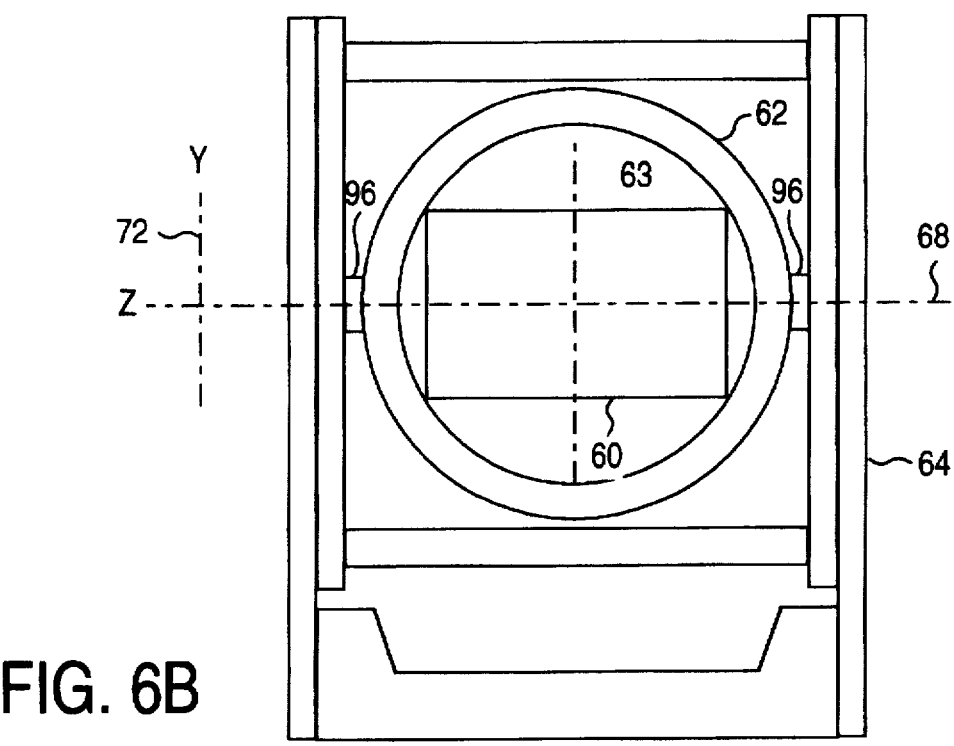
Figure 6C:
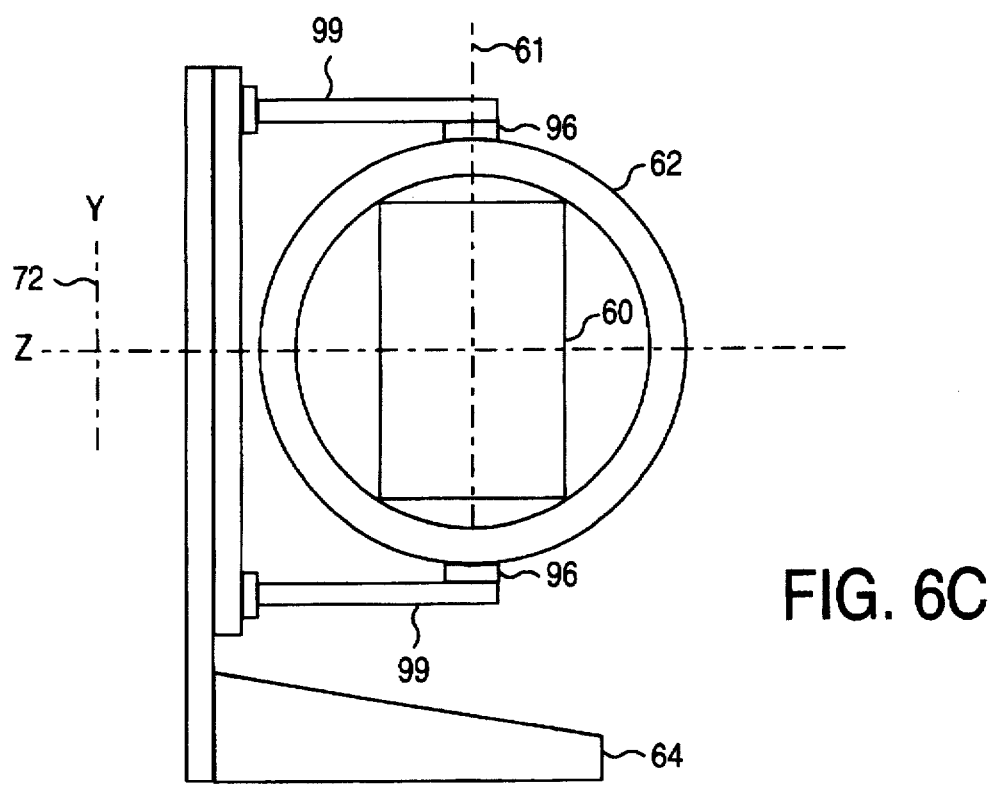
FIG. 6C illustrates a detector head supported by a cantilevered thin-section bearing.

FIGS. 6A through 6C illustrate another embodiment of the present invention which provides a mechanism for pivoting a gamma camera detector head about its centroid to increase the field of view in the z direction. A rectangular detector head 60 has a long axis 61 parallel to its longer sides and a short axis 63 parallel to its shorter sides. The detector head 60 is typically oriented during imaging with the long axis 61 perpendicular to the z axis 68, as shown in FIG. 6A. However, in situations in which higher throughput is needed, the detector head 60 can be reoriented so that the short axis 63 is perpendicular to the z axis 68, as shown in FIG. 6B. The orientation shown in FIG. 6B provides a larger field of view along the z axis than the orientation shown in FIG. 6A, so that more data can be gathered in the z direction in a given period of time.

The capability to reorient the detector head 60 is provided by mounting the detector head 60 to a thin-section bearing 62. Thin-section bearing 62 is coupled to the gantry 64 in a manner which permits the entire bearing 62 to be rotated about the z axis. In one embodiment, bearing 62 is coupled at diametrically opposite points by two support arms 96 to a pair of ring gears (not shown). If desired, two or more bearings can be provided to support two or more detector heads that can be reoriented as described above. In an alternative embodiment, shown in FIG. 6C, the bearing 62 is coupled to a single ring gear (not shown), in a manner similar to that described with reference to FIGS. 3 and 4. Specifically, the bearing is coupled to the ring gear by two support arms 99. It should be appreciated that some form of counterbalance may be required to offset the weight of the detector head 60 and bearing 62 that is applied to the ring gear.

FIGS. 7A and 7B show thin-section bearing 62 in greater detail. Bearing 62 is ring-shaped and has a large diameter relative to its width and thickness. Such a bearing is manufactured by Kaydon Corporation, of Muskegon, Mich. A bearing of this type is suitable for supporting both the radial and thrust direction loading that occurs as a detector head is rotated around a patient. Bearing 62 comprises an inner support ring 90 rotatably coupled to an outer support ring 92. Inner support ring 90 is concentric with outer support ring 92 and has an inner diameter which is just large enough to support detector head 60 at the corners 97. The detector head 60 may be constructed to have tapered corners to allow a smaller diameter bearing to be used, as illustrated in FIG. 7C.

Detector head 60 is coupled to inner support ring 90 by a solid metal plate 103 attached to the detector head 60 along each side of the detector head 60 and attached to inner support ring 90 along its inner circumference. Metal plate 103 serves to distribute the load applied to the inner support ring 90. In an alternative embodiment illustrated in FIG. 7D, the detector head 60 is supported by a number of support struts 101 coupled to inner support ring 90. It should be appreciated that the detector head 60 may be coupled to inner support ring 90 in other ways within the scope of the present invention.

Inner support ring 90 has an outer diameter which is approximately equal to the inner diameter of outer support ring 92, so that inner support ring 90 is rotatable about an axis 94 passing through the centroid of the detector head 60. Two manual locks 82 are provided on bearing 62 at positions 90 degrees apart (measured about axis 94) in order to lock the inner support ring 90 to the outer support ring 92. Accordingly, the detector head 60 can be locked in the orientation of FIG. 6A or the orientation of FIG. 6B. The outer support ring 92 is coupled to the two support arms 96, each of which is mounted to one of two ring gears 98. The ring gears 98 are rotatable about the z axis 68, thus allowing the detector head 60 to be rotated about the z axis.

Figure 8:
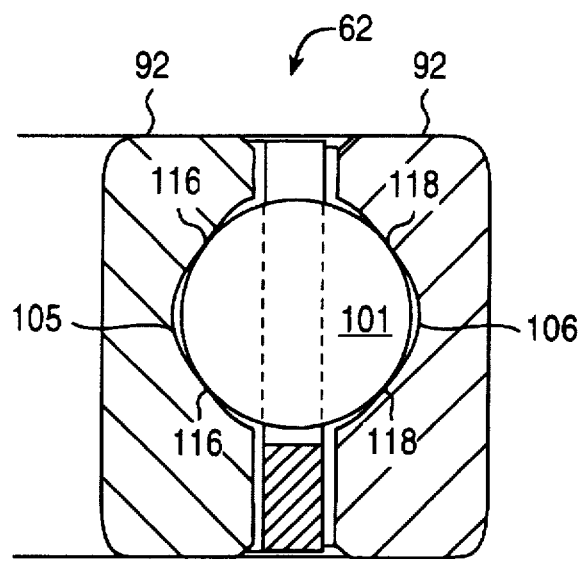
FIG. 8 shows a cross-sectional view of a thin-section bearing.

FIG. 8 shows a cross-sectional view of bearing 62. The inner support ring 90 has a rounded groove 105 in its outer circumferencial surface, while the outer support ring 92 has a matching groove 106 in its inner circumferencial surface. Grooves 105 and 106 accommodate a number of balls 101, which allow the inner support ring 90 to rotate with respect to the outer support ring 92. Each ball 101 contacts the inner support ring 90 at two points 116 and contacts the outer support ring 92 at two points 118.

Figure 9:
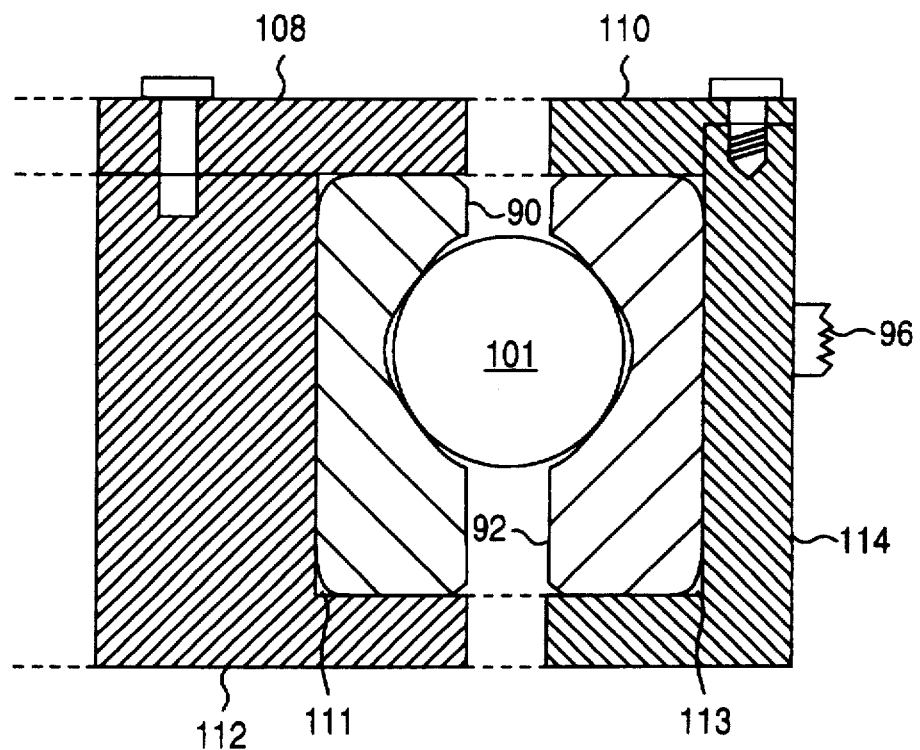
FIG. 9 shows a cross-sectional view in which a thin-section bearing is supported by two secondary support rings.

It should be appreciated that the thin-section bearing 62 may require additional support to prevent warping or deflection due to uneven loads. FIG. 9 illustrates one embodiment providing such support. The ring bearing 62, which comprises inner support ring 90 and outer support ring 92, is supported by two secondary support rings 112 and 114. Specifically, inner support ring 90 is support by secondary support ring 112, while outer support ring 92 is supported by secondary support ring 114. Inner support ring 90 fits into an "L"-shaped notch 111 in secondary support ring 112 and is held in place by clamp plate 108, which is bolted, screwed, or otherwise fixed to secondary support ring 112. Outer support ring 92 fits into "L"-shaped notch 113 in secondary support ring 114 and is held in place by clamp plate 110, which is bolted, screwed, or otherwise fixed to secondary support ring 114. In the embodiment of FIG. 9, support arm 96 is coupled to secondary support ring 114, rather than directly to outer support ring 92. Also, in the embodiment of FIG. 9, locks 82 (see FIG. 7B) could be configured to fix secondary support ring 112 to secondary support ring 114, rather then to directly fix inner support ring 90 to outer support ring 92.

Thus, a dual-head medical imaging system with cantilevered detector heads has been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A multi-head medical imaging system, comprising:
   a support structure;
   a master ring gear rotatably supported by the support structure, such that the master ring gear is rotatable about a longitudinal axis;
   a first detector head;

a first support member coupled to the master ring gear and supporting the first detector head, such that the first detector head is supported entirely through the first support member;

a slave ring rotatably coupled to and supported by the master ring gear;

a second detector head; and a second support member coupled to the slave ring and supporting the second detector head, such that the second detector head is supported entirely through the second support member, wherein the master ring gear and the slave ring are rotatable about the longitudinal axis either independently or in unison, such that the first detector head and the second detector head are moveable in rotation about the longitudinal axis relative to each other.

2. A multi-head medical imaging system according to claim 1, wherein the first detector head and the second detector head are rotatable about the longitudinal axis through a range of relative angular displacements from 180 degrees to 90 degrees.

3. A multi-head medical imaging system according to claim 1, further comprising a clutch mechanism for holding one of the master ring gear or the slave ring stationary while allowing the other to rotate about the longitudinal axis.

4. A multi-head medical imaging system according to claim 1, wherein the first support member is slidably coupled to the master ring gear, such that the first detector head is moveable toward or away from the longitudinal axis.

5. A multi-head medical imaging system according to claim 4, wherein the second support member is slidably coupled to the slave ring, such that the second detector head is moveable toward or away from the longitudinal axis.

6. A multi-head gamma camera system, comprising:

a support structure;

a master ring rotatably supported by the support structure, such that the master ring is centered on and rotatable about a longitudinal axis;

a first detector head;

a first cantilever support coupled to the master ring and supporting the first detector head;

a slave ring rotatably coupled to and supported by the master ring, the slave ring being concentric with the master ring, such that the slave ring is rotatable about the longitudinal axis;

a second detector head; and a second cantilever support coupled to the slave ring and supporting the second detector head, wherein the first detector head and the second detector head are moveable in rotation about the longitudinal axis relative to each other.

7. A multi-head gamma camera system according to claim 6, wherein the first detector head and the second detector head each have an imaging surface, and wherein the first detector head and the second detector head are rotatable about the longitudinal axis into a relative orientation in which the imaging surface of the first detector defines a plane that is perpendicular to a plane defined by the imaging surface of the second detector.

8. A multi-head gamma camera system according to claim 6, further comprising a locking mechanism for holding either the master ring or the slave ring stationary while allowing the other one of the master ring and the slave ring to rotate about the longitudinal axis.

9. A multi-head gamma camera system according to claim 8, further comprising a motor for rotating the master ring and the slave ring, wherein the locking mechanism comprises a clutch brake coupled to the motor and to both the master ring and the slave ring.

10. A multi-head gamma camera system according to claim 6, wherein the first cantilever support is slidably coupled to the master ring, such that the first detector head is moveable toward or away from the longitudinal axis.

11. A multi-head gamma camera system according to claim 10, wherein the second cantilever support is slidably coupled to the slave ring, such that the second detector head is moveable toward or away from the longitudinal axis.

12. A multi-head gamma camera system according to claim 6, wherein the first detector head has a detector axis substantially parallel to the longitudinal axis and passing approximately through a centroid of the first detector head, and wherein the first detector head is rotatably coupled to the first cantilever support, such that the first detector head is rotatable about the detector axis.

13. A multi-head gamma camera system according to claim 12, wherein the second detector head has a detector axis substantially parallel to the longitudinal axis and passing approximately through a centroid of the second detector head, and wherein the second detector head is rotatably coupled to the second cantilever support, such that the second detector head is rotatable about the detector axis.

14. A multi-head gamma camera system according to claim 6, wherein the first detector head has an imaging surface and an axis of rotation passing through the imaging surface perpendicular to the imaging surface, and wherein the first cantilever support comprises:

a first support ring;

a second support ring concentric with the first support ring and rotatably coupled to the first support ring, the second support ring having an outer diameter substantially equal to an inner diameter of the first support ring, wherein the detector head is mounted to an inner diameter of the second support ring, such that the first detector head is rotatable about the axis of rotation.

15. A multi-head gamma camera system according to claim 6, wherein the second detector head has an imaging surface and an axis of rotation passing through the imaging surface perpendicular to the imaging surface, the second detector head further having a plurality of corners, and wherein the second cantilever support comprises:

a first support ring;

a second support ring concentric with the first support ring and rotatably coupled to the first support ring, the second support ring having an outer diameter substantially equal to an inner diameter of the first support ring, wherein the detector head is mounted to an inner diameter of the second support ring by the corners, such that the second detector head is rotatable about the axis of rotation.

16. A support apparatus for an imaging system detector head, the detector head having an imaging surface, the support apparatus comprising:

a first support ring; and a second support ring concentric with the first support ring and rotatably coupled to the first support ring, wherein the detector head is mounted to the second support ring, such that the detector is rotatable about an axis of rotation passing through the imaging surface substantially perpendicular to the imaging surface.

17. A support apparatus according to claim 16, wherein the detector head further comprises a plurality of edges perpendicular to the imaging surface, the support apparatus further comprising means for mounting the detector head to the second support ring at the edges, such that the detector is rotatable about the axis of rotation.

18. A support apparatus according to claim 16, further comprising locking means for locking the inner support ring to the outer support ring such as to prevent relative rotation between the inner support ring and the outer support ring.

19. A support apparatus according to claim 18, wherein the detector head is rotatable around and offset from a longitudinal axis of an object to be imaged, wherein the detector head has a long axis, and wherein the locking means is further for locking the inner support ring in a first position wherein the long axis is perpendicular to the longitudinal axis of the object to be imaged or in a second position wherein the long axis is parallel to the longitudinal axis of the object to be imaged.

20. A support apparatus according to claim 18, wherein the locking means comprises:
   a first lock coupled to the outer support ring for fixedly coupling the outer support ring to the inner support ring; and
   a second lock coupled to the outer support ring for fixedly coupling the outer support ring to the inner support ring, wherein the angular displacement about a center of the outer support ring between the first lock and the second lock is 90 degrees.

21. A support apparatus according to claim 16, wherein the second support ring has an outer diameter substantially equal to an inner diameter of the first support ring.

22. A support apparatus according to claim 16, wherein the second support ring is rotatable about the axis of rotation relative to the first support ring.

23. A support structure for a gamma camera system, the support structure comprising:
   a gantry;
   a bearing coupled to the gantry, the bearing comprising:
      a first support ring coupled to the gantry; and
      a second support ring concentric with the first support ring and rotatably coupled to the first support ring, the second support ring having an outer diameter substantially equal to an inner diameter of the first support ring;
   a detector head coupled to the second support ring, the detector head having an imaging surface and an axis of rotation passing through the imaging surface perpendicular to the imaging surface, the detector head further having a cross section characterized by a plurality of vertices, wherein the detector head is mounted to the second support ring at said vertices, such that the detector is rotatable about the axis of rotation; and
   means for rotating the bearing about a longitudinal axis.

24. A support structure according to claim 23, wherein the means for rotating comprises a circular ring gear having the detector assembly mounted thereto, wherein the ring gear is rotatably coupled to the gantry and centered on the longitudinal axis, such that the ring gear is rotatable about the longitudinal axis.

25. A support structure according to claim 23, wherein the detector head has a long axis, and wherein the second support ring is rotatable about the axis of rotation between a first position in which the long axis is perpendicular to the longitudinal axis and a second position in which the long axis is parallel to the longitudinal axis.

26. A support structure according to claim 23, further comprising:
   a ring gear rotatably supported by the support structure, such that the ring gear is centered on and rotatable about the longitudinal axis;
   a cantilevered support arm coupling the bearing to the ring gear, such that the bearing is entirely supported through the cantilevered support arm.

27. A medical imaging system, comprising:
   a support structure;
   a rotating member supported by the support structure, such that the rotating member is centered upon and rotatable about a longitudinal axis;
   a detector head;
   a support arm coupled to the rotating member and rotatably supporting the detector head, such that the detector head is radially displaced from the longitudinal axis, the support arm supporting the detector head such that the detector head is rotatable about an axis of rotation passing through the detector head parallel to the longitudinal axis, wherein the axis of rotation is displaced from a center of mass of the detector head; and
   a locking mechanism for selectively preventing the detector head from rotating about the axis of rotation, such that a rotation of the rotating member about the longitudinal axis while the locking mechanism is disengaged causes a gravitational moment to be applied to the detector head about the axis of rotation to cause the detector head to rotate about the axis of rotation.

28. In a medical imaging system having a detector head, the detector head having an imaging surface, the detector head being rotatable along a curved path about a longitudinal axis, the detector head further being rotatable about an axis of rotation passing through the detector head parallel to the longitudinal axis, the imaging system having a locking mechanism for preventing rotation of the detector head about the axis of rotation, a method of reorienting the detector head, the method comprising the steps of:
   positioning the detector head in a first position along the curved path;
   disengaging the locking mechanism; and
   rotating the detector head about the longitudinal axis along the curved path to a second position on the curved path, such that the detector head rotates about the axis of rotation passing through the detector head in response to a gravitational moment applied about the axis of rotation during said rotation, such that the imaging surface faces away from the longitudinal axis while the detector head is in the second position.

29. A method according to claim 28, wherein in the rotating step, the detector head is rotated such that, in the second position, the imaging surface is positioned to be substantially vertical.

* * * * *